(12) United States Patent
Truong et al.

(10) Patent No.: US 8,170,692 B2
(45) Date of Patent: May 1, 2012

(54) IMPLANT TOOL FOR ACTIVE FIXATION LEAD

(75) Inventors: Frank Truong, El Monte, CA (US); Virote Indravudh, Santa Clarita, CA (US); Shimul Sengupta, Chatsworth, CA (US); Jayaram Sundararajan, Minnetonka, MN (US); Elizabeth Nee, Chicago, IL (US); Ryan Buesseler, Fergus Falls, CA (US)

(73) Assignee: Pacesetter, Inc., Sylmar, CA (US)

( * ) Notice: Subject to any disclaimer, the term of this patent is extended or adjusted under 35 U.S.C. 154(b) by 231 days.

(21) Appl. No.: 12/697,020

(22) Filed: Jan. 29, 2010

(65) Prior Publication Data

US 2010/0137878 A1 Jun. 3, 2010

Related U.S. Application Data

(62) Division of application No. 11/468,069, filed on Aug. 29, 2006, now abandoned.

(51) Int. Cl.
*A61N 1/05* (2006.01)

(52) U.S. Cl. ........................................ 607/127; 607/116

(58) Field of Classification Search .................... 607/127
See application file for complete search history.

(56) References Cited

U.S. PATENT DOCUMENTS

| | | | |
|---|---|---|---|
| 3,737,579 A | 6/1973 | Bolduc | |
| 3,875,947 A | 4/1975 | Jula et al. | |
| 4,209,019 A | 6/1980 | Dutcher et al. | |
| 5,228,455 A | 7/1993 | Barcel | |
| 5,741,321 A | 4/1998 | Brennen | |
| 6,010,526 A | 1/2000 | Sandstrom et al. | |
| 6,629,981 B2 * | 10/2003 | Bui et al. | 606/108 |
| 6,687,550 B1 | 2/2004 | Doan | |
| 2006/0253179 A1 | 11/2006 | Goode et al. | |

OTHER PUBLICATIONS

Restriction Requirement, mailed Dec. 24, 2006—Parent Case U.S. Appl. No. 11/648,069.
NonFinal Office Action, mailed Jan. 30, 2009—Parent Case U.S. Appl. No. 11/648,069.
Final Office Action, mailed Oct. 2, 2009—Parent Case U.S. Appl. No. 11/648,069.
Advisory Action, mailed Jan. 21, 2010—Parent Case U.S. Appl. No. 11/648,069.

* cited by examiner

Primary Examiner — Michael Kahelin

(57) ABSTRACT

An implant tool for use with an endocardial or other implantable lead having an extendable/retractable active fixation tip includes a housing, a shaft rotatably supported by the housing, and a shaft rotation mechanism for rotating the shaft through a predetermined angular travel. The shaft includes a lead attachment portion for selectively coupling a lead to the shaft such that the lead is rotatable with the shaft. The implant tool may include a control tab slidably supported by the housing, wherein longitudinal movement of the control tab actuates the shaft rotation mechanism. The shaft rotation mechanism may include a gear train, an electric motor, a double acting spring mechanism, or a retractable tape wound around the shaft. The gear train includes an input member coupled to the control tab and an output gear coupled to the shaft. The input member meshes with an input gear supported by the housing.

3 Claims, 10 Drawing Sheets

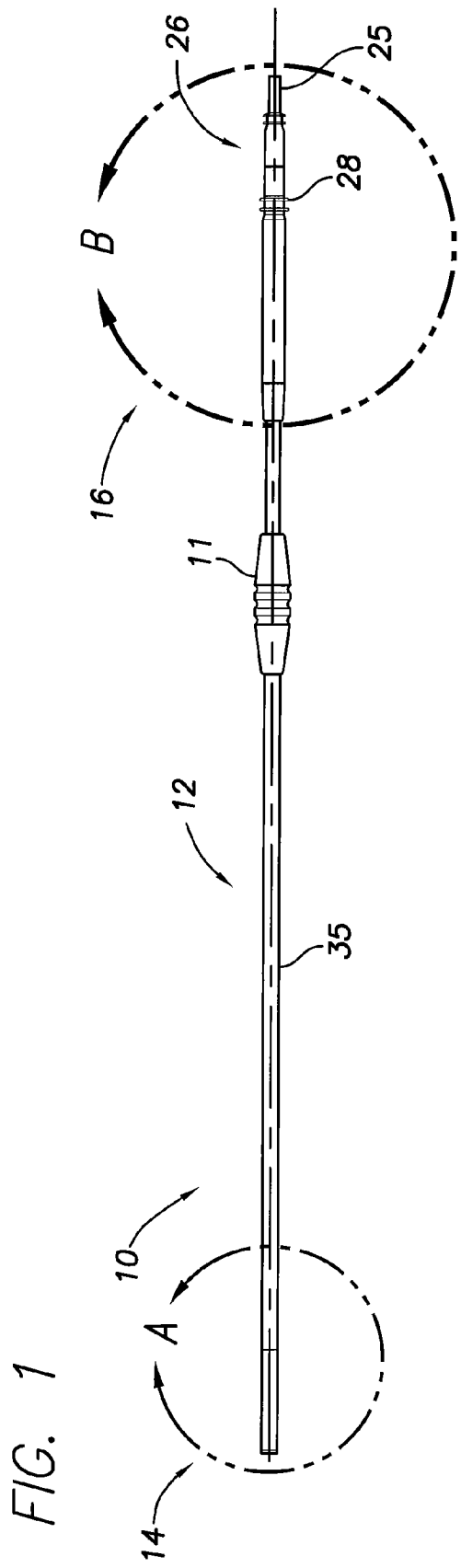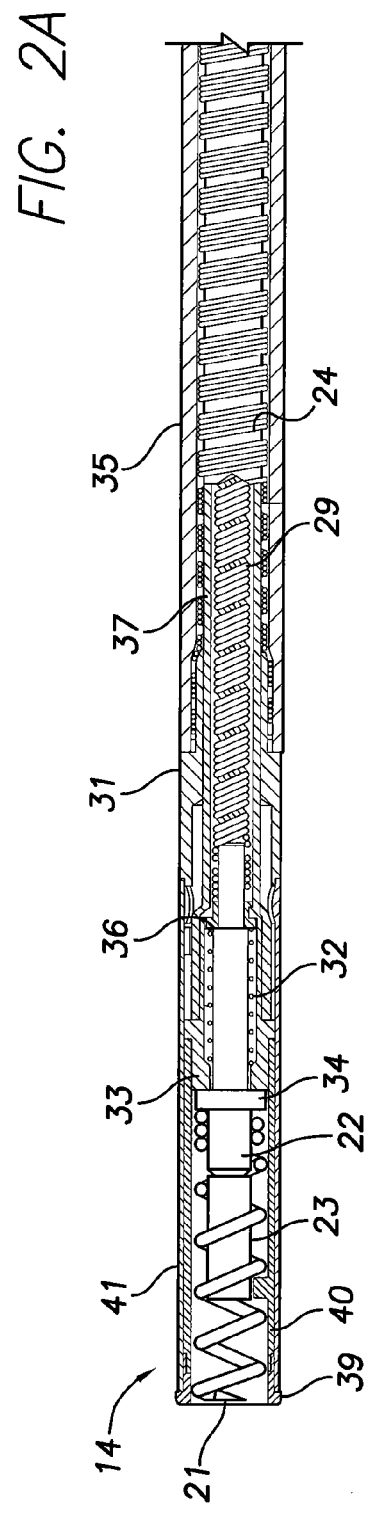

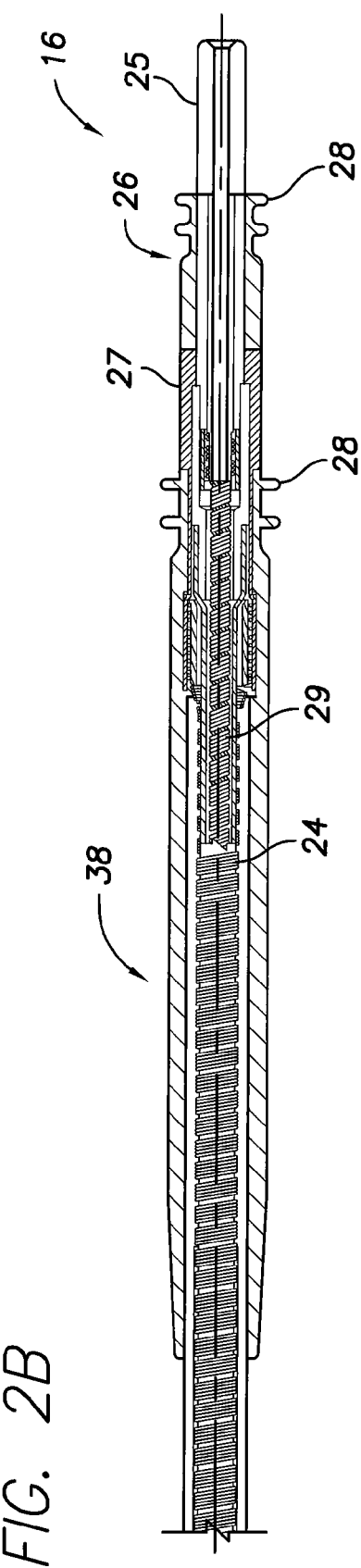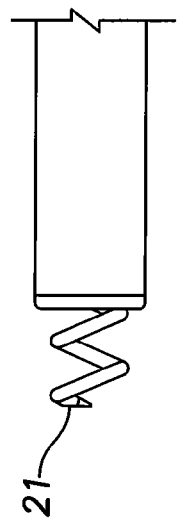

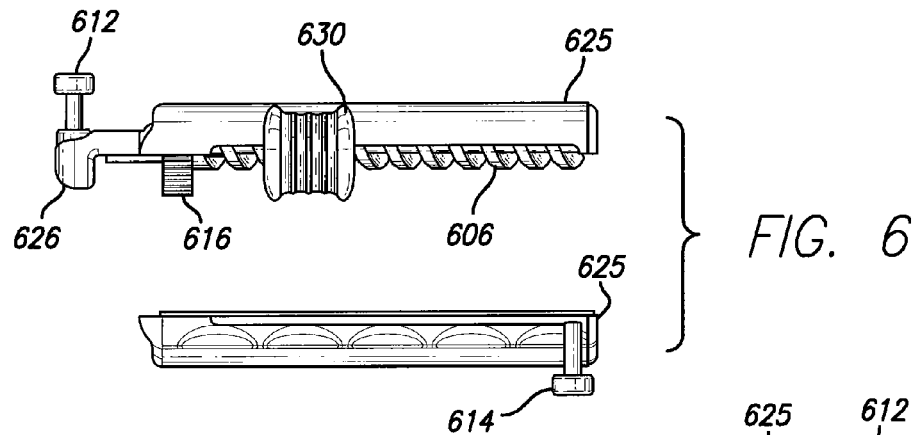
FIG. 6
FIG. 6A
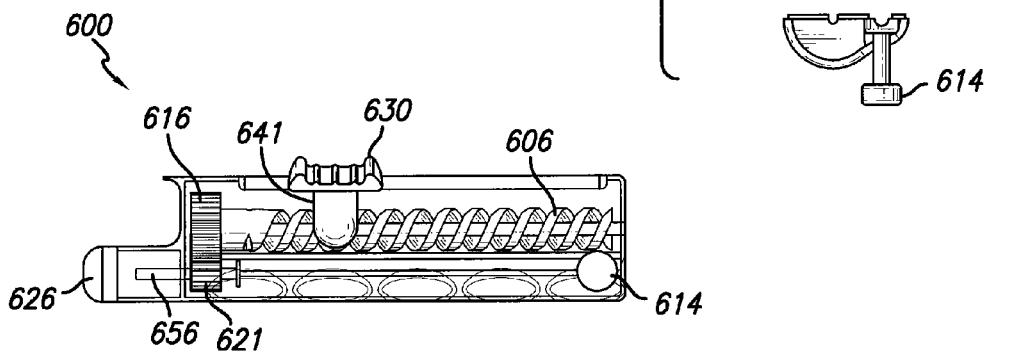
FIG. 6B
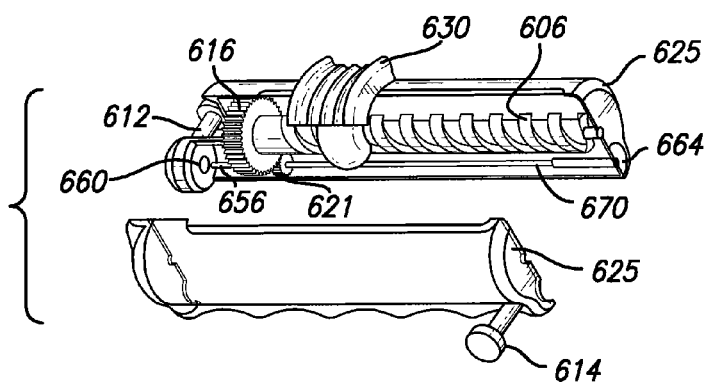
FIG. 6C

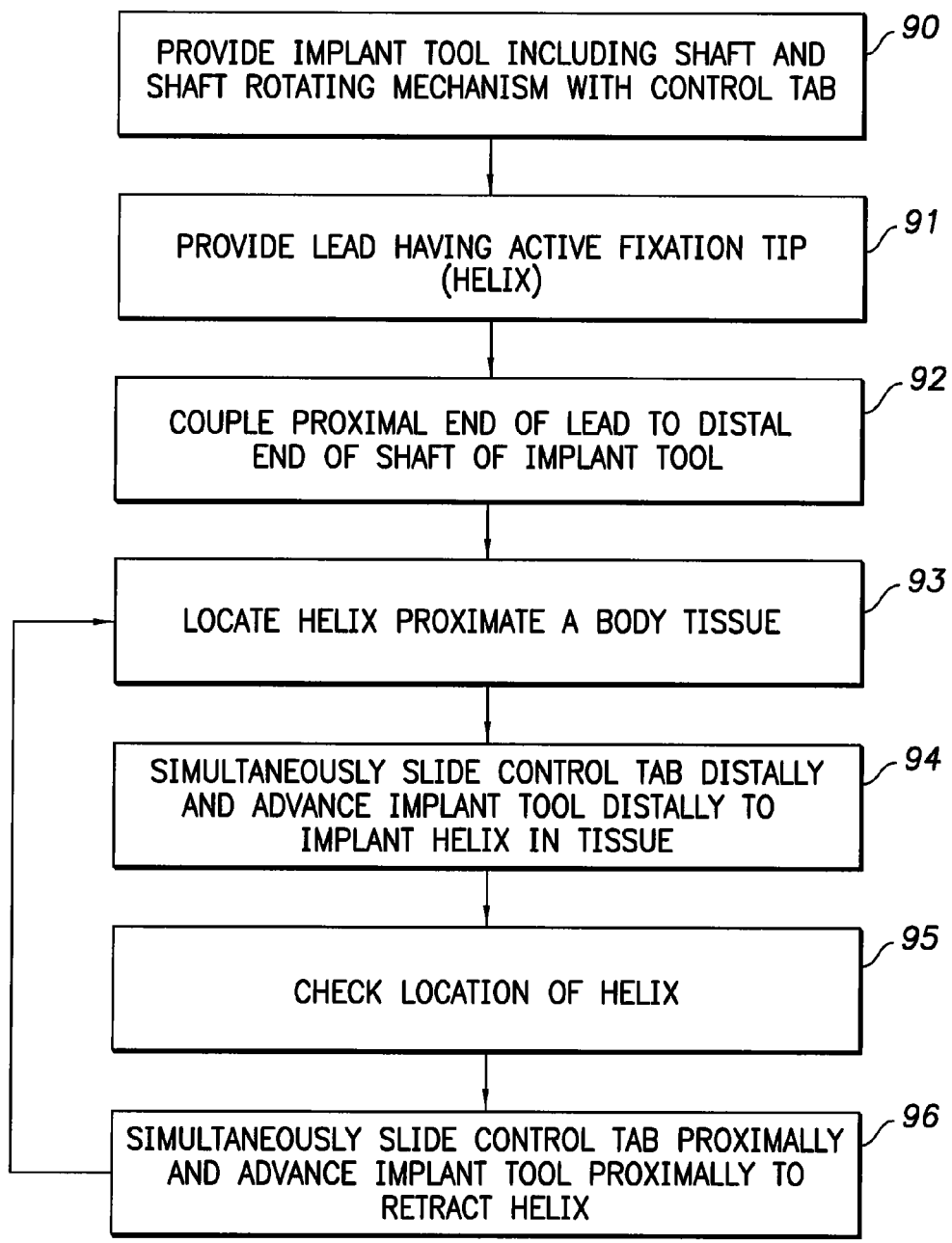

IMPLANT TOOL FOR ACTIVE FIXATION LEAD

CROSS REFERENCE TO RELATED APPLICATIONS

This application is a division of U.S. patent application Ser. No. 11/468,069, filed Aug. 29, 2006.

FIELD OF THE INVENTION

The present invention relates to an implant tool for implanting a tissue-stimulating lead having an active fixation tip, such as an endocardial lead having an extendable/retractable screw-in (helix) tip.

BACKGROUND OF THE INVENTION

A body-implantable lead is used with an implantable cardiac device (ICD), such as an implantable pacemaker, a cardioverter, a defibrillator, a cardioverter defibrillator, and the like, to both sense cardiac function and deliver stimulation pulses to a desired tissue location. When the stimulating device is a cardiac pacemaker, for example, the lead, also referred to as a "pacing lead," connects the pacemaker's electrical circuitry directly with a desired chamber of the heart. One or more electrodes at or near a distal end of the lead placed inside of the heart contact the cardiac tissue therein at the desired location. The electrode(s) are electrically connected via insulated conductors within the lead to an appropriate connector at a proximal end of the lead. After an implantable lead is transvenously or otherwise implanted at the proper tissue location, the connector at the proximal end of the lead is detachably inserted into an appropriate mating connector of a medical device, such as a pacemaker, thereby electrically coupling the desired tissue location to the electrical circuits within the medical device.

The distal tip of the implantable lead is held at a desired tissue location by either active fixation or passive fixation. Active fixation (sometimes called "positive fixation") involves the use of some type of mechanism or means, such as a helix or hook, for actively securing and holding the body tissue in contact with the distal tip. The most common type of active fixation is achieved using a screw-in helix tip located at the distal end of the lead. Active fixation is achieved by literally screwing the helix tip into the tissue. In contrast, passive fixation involves use of some type of mechanism or means, such as a tine assembly near the distal electrode, to lodge or passively fix the lead inside the heart. Tissue ingrowth can occur into the lead tip in order to firmly hold it in its desired position.

A common technique used to implant an active fixation lead is to insert the lead transvenously into the desired tissue contact location, e.g., inside of the heart. However, such transvenous insertion requires that the active fixation tip be maintained in a retracted position until the distal tip of the lead is at the desired tissue contact location. Otherwise, during the process of inserting the lead, the active fixation tip, comprising, e.g., a sharp, protruding screw-in helix tip, could easily become entangled with and/or damage delicate body tissue at a location other than the desired tissue contact location. Thus, many active fixation leads have extendable/retractable helix tips which may be retracted within or extended from the lead body, thereby allowing the helix tip to be shielded during implantation and exposed during fixation. A simple construction of such a lead incorporates a connector pin attached to a conductor coil of the lead that is in turn attached to a fixation helix. In order to extend the helix and anchor it into the heart tissue, a clip-on tool or implant tool is used to rotate the connector pin. Rotation of the connector pin rotates the conductor coil, which in turn rotates the fixation helix, thereby causing it to extend or retract. Many existing implant tools require the surgeon to count the number of rotations to achieve proper rotation of the connector pin. Many active fixation leads require about ten rotations of the connector pin to extend or retract the helix. Proper rotation of the connector pin is required to ensure fixation of the lead to the heart tissue, since excessive rotations can damage the connection between the helix and the coil or result in perforation, while too few rotations can result in improper fixation.

What is needed, therefore, is an implant tool for a lead, and method of using the same, that facilitates proper rotation of the connector pin to ensure fixation of the active fixation tip to the body tissue.

BRIEF SUMMARY

A lead extension and retraction device for implanting an extendable/retractable active fixation lead is presented. The lead extension and retraction device, or implant tool, includes a housing, a shaft rotatably supported by the housing, and a shaft rotation mechanism for rotating the shaft through a predetermined angular travel. The shaft includes a lead attachment portion for selectively coupling a lead to the shaft such that the lead is rotatable with the shaft. In one embodiment, the implant tool has a control tab slidably supported by the housing. Longitudinal movement of the control tab actuates the shaft rotation mechanism. In another embodiment, the control tab is slidable over a predetermined distance, and the shaft rotation mechanism is a gear train for rotating the shaft through the predetermined angular travel that is limited by the sliding distance of the control tab. The gear train includes an input member coupled to the control tab and an output gear coupled to the shaft. The input member meshes with an input gear supported by the housing.

In another embodiment, the shaft rotation mechanism includes an electric motor configured to rotate the shaft through the predetermined angular travel.

In another embodiment, the shaft rotation mechanism includes a double acting spring mechanism and an actuation mechanism. The double acting spring mechanism includes a right hand wound spring, a left hand wound spring, and a slider. The actuation mechanism is configured to release the right hand wound spring and the left hand wound spring alternately to rotate the shaft in opposite directions.

In another embodiment, the shaft rotation mechanism includes a retractable tape positioned within the housing and wound around the shaft. The tape is configured to unwind from and rotate the shaft in a first direction when the tape is pulled through an opening in the housing, and rotate the shaft in a second, opposite direction when the tape is retracted.

BRIEF DESCRIPTION OF THE DRAWINGS/FIGURES

The accompanying drawings, which are incorporated herein and form part of the specification, illustrate the apparatus and methods presented herein, and together with the description, the drawings further serve to explain the principles of and to enable a person skilled in the relevant art(s) to make and use the apparatus and methods presented herein. In the drawings, like reference numbers indicate identical or functionally similar elements.

FIG. 1 is a side elevation view of an exemplary body-implantable lead which may be employed with an embodiment of an implant tool presented herein.

FIG. 2A is a longitudinal cross section view of section "A" at a distal end of the lead illustrated in FIG. 1 showing an electrode assembly having an active fixation distal tip, showing the active fixation tip in its retracted position.

FIG. 2B is a longitudinal cross section view of section "B" at a proximal end of the lead illustrated in FIG. 1 showing a connector assembly.

FIG. 2C is a side elevation view of the distal end of the lead of FIG. 2A showing the active fixation tip in its extended position.

FIG. 6 is a top elevation view of an implant tool according to a fourth embodiment presented herein, wherein a half of a housing is detached.

FIG. 6A is a front perspective view of the implant tool shown in FIG. 6.

FIG. 6B is a side elevation view (with interior parts visible) of the implant tool shown in FIG. 6.

FIG. 6C is a side perspective view of the implant tool shown in FIG. 6, wherein the half of the housing is detached to show interior parts.

FIG. 9 is a flowchart illustrating steps performed in a method of implanting the active fixation tip using an embodiment of the implant tool presented herein.

DETAILED DESCRIPTION OF THE INVENTION

Figure 3:
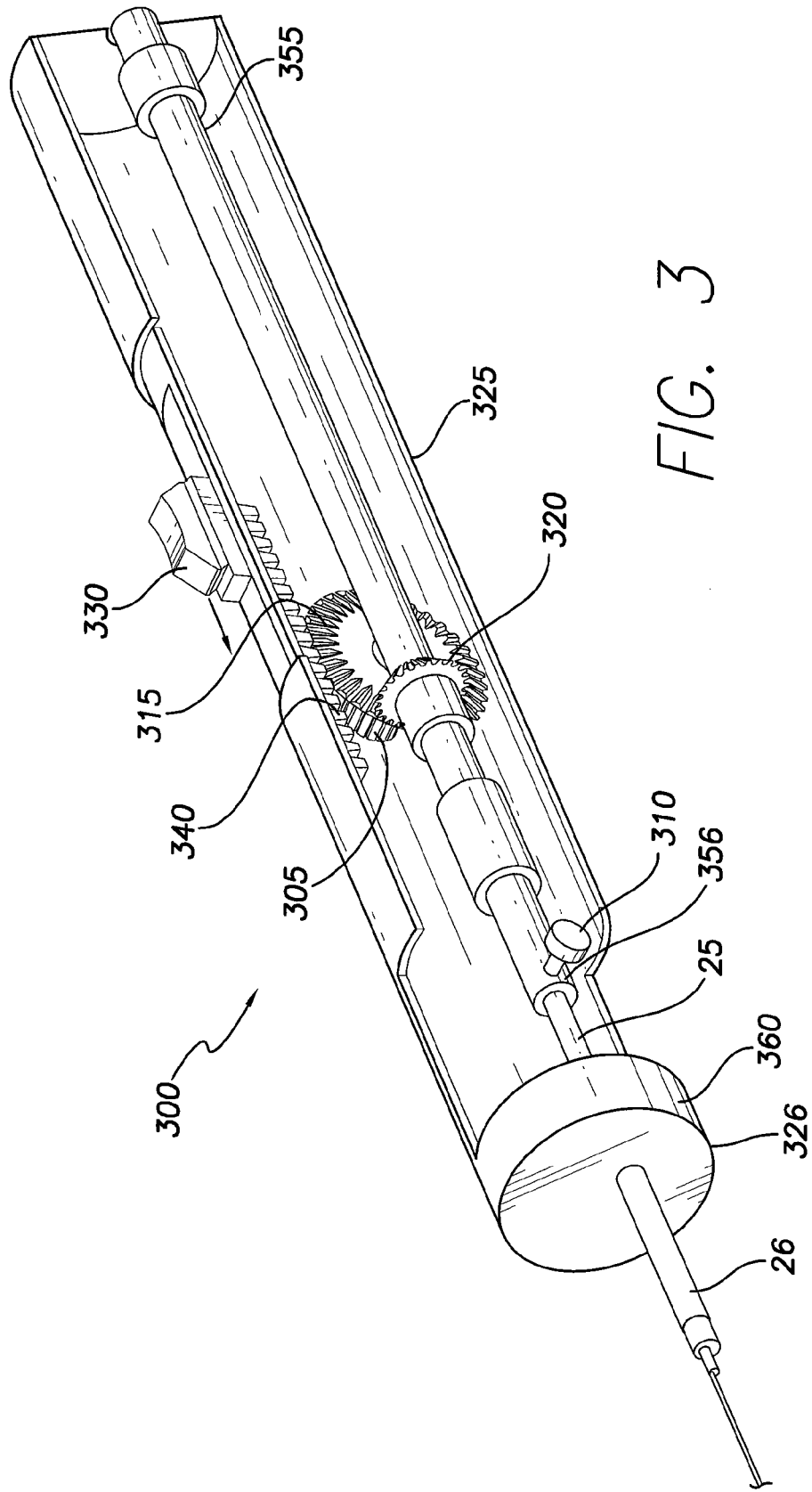
FIG. 3 is a side perspective view, in partial cutaway, of an implant tool according to a first embodiment presented herein.

FIG. 1 shows an exemplary body-implantable lead 10 which may be employed with an embodiment of an implant tool presented herein. Lead 10 is designed for intravenous insertion and contact with the endocardium, and therefore may be conventionally referred to as an endocardial lead. Lead 10 has a distal end 14 and a proximal end 16 and is provided with an elongated lead body 12, which includes electrical conductors (not shown in this view) covered with an outer insulation sleeve or sheath 35. The outer insulation sleeve 35 may be fabricated of any insulative material, such as silicone rubber, polyurethane or other biocompatible plastic. A suture sleeve 11, slidably mounted around lead body 12, serves to stabilize lead 10 at the site of venous insertion. At proximal end 16 of lead 10 is a connector assembly which includes a connector boot 26, a connector pin 25, and sealing rings 28. The connector assembly is described in further detail below with reference to FIG. 2B.

FIG. 2A illustrates a longitudinal cross section view of section "A" at distal end 14 of lead 10 illustrated in FIG. 1. At distal end 14 is an electrode assembly having a helical electrode with active fixation distal tip or helix 21. Helix 21 is electrically coupled to an inner conductor coil 29, which terminates at proximal end 16 of lead 10 at connector pin 25. Helix 21 may be fabricated of any biocompatible conductor, such as stainless steel or platinum alloy. Helix 21 is movable between a retracted position (FIG. 2A) fully within lead body 12 and an extended position (FIG. 2C) extended beyond distal end 14 of lead 10 for effecting penetration into the myocardial tissue.

Lead 10 may include an electrically active lead housing 40 at distal end 14 of lead 10 terminating distally at an electrically active collar 39 which is coaxial with helix 21. A sleeve 41 of silicone rubber or other suitable dielectric material overlies electrically active housing 40, leaving exposed collar 39. Collar 39 permits testing the suitability of an implantation site without necessarily having to extend the helix to verify the pacing threshold and sensing amplitude. To this end, lead 10 may further include a resilient coupling mechanism for maintaining electrical contact between the helix electrode and the electrically active housing throughout movement of helix 21 between its retracted and extended positions. Such a resilient coupling mechanism is described in U.S. Pat. No. 6,687,550, which is incorporated herein by reference in its entirety.

As illustrated in FIG. 2A, the coupling mechanism includes a conductive coupling 33 suitably fixed to electrically active housing 40 and slidably received on a conductive shaft 22 to which helix 21 is welded or otherwise connected. Inner conductor coil 29 is welded or otherwise fixed to a proximal end of conductive shaft 22. A compression spring 32 is engaged with a base of conductive coupling 33 on one end and on its other end with a conductive stopper 36 integral with conductive shaft. An annular collar 34 is integral with conductive shaft 22 at an intermediate location toward a distal end of conductive shaft and projects radially from the longitudinal axis and beyond an outer surface of conductive shaft 22. Annular collar 34 is engaged with a distal terminal surface of conductive coupling 33 when helix 21 is in the retracted position and is spaced from the distal terminal surface of conductive coupling 33 (not shown) when helix 21 is in the extended position.

Inner conductor coil 29 is covered by an inner insulation sleeve 37. Lead 10 may also include an outer conductor coil 24 covered by outer insulation sleeve 35 with a ring electrode 31 spaced from distal end 14 of lead 10 and electrically connected with outer conductor coil 24. Hence, lead body 12 includes inner coiled conductor 29 covered by inner insulation sleeve 37, which is in turn covered by outer coiled conductor 24, which is covered by outer insulation sleeve 35.

Lead 10 is also constructed to include a hollow interior extending from proximal end 16 to distal end 14. The hollow interior is of a size to allow for the introduction of a stylet (guidewire) during implant, which is beneficial in allowing the surgeon to guide the otherwise flexible lead 10 from the point of venous insertion to the myocardium. A typical stylet diameter is 0.016 inches or about 0.41 millimeters.

Lead 10 may also include a therapeutic element or steroid plug 23 formed of a biocompatible matrix material and generally cylindrical in shape coaxial with and integral with helix 21. The therapeutic element 23 may be of a known design and composition.

FIG. 2B is a longitudinal cross section view of section "B" including the connector assembly at proximal end 16 of lead 10 illustrated in FIG. 1. Connector assembly includes connector pin 25 extending into connector boot 26. Connector boot 26 is preferably formed from a biocompatible plastic or elastomeric material such as, for example, silicone rubber, and may include a plurality of sealing rings 28 and a connector grip area 38 extending a short distance from connector pin 25. Connector pin 25 is electrically coupled to inner conductor coil 29, and is also mechanically coupled such that rotation of connector pin 25 in a first direction causes helix 21 to rotate in the first direction, and rotation of connector pin 25 in a second, opposite direction causes helix 21 to rotate in the second direction. Connector pin 25 may be fabricated of stainless steel or other suitable electrically conductive material. Disposed between sealing rings 28 is a connector ring 27 which is electrically coupled to outer conductor coil 24. The entire connector assembly may be a few inches or less in length, with a typical length of about 1.75 inches.

Figure 3A:
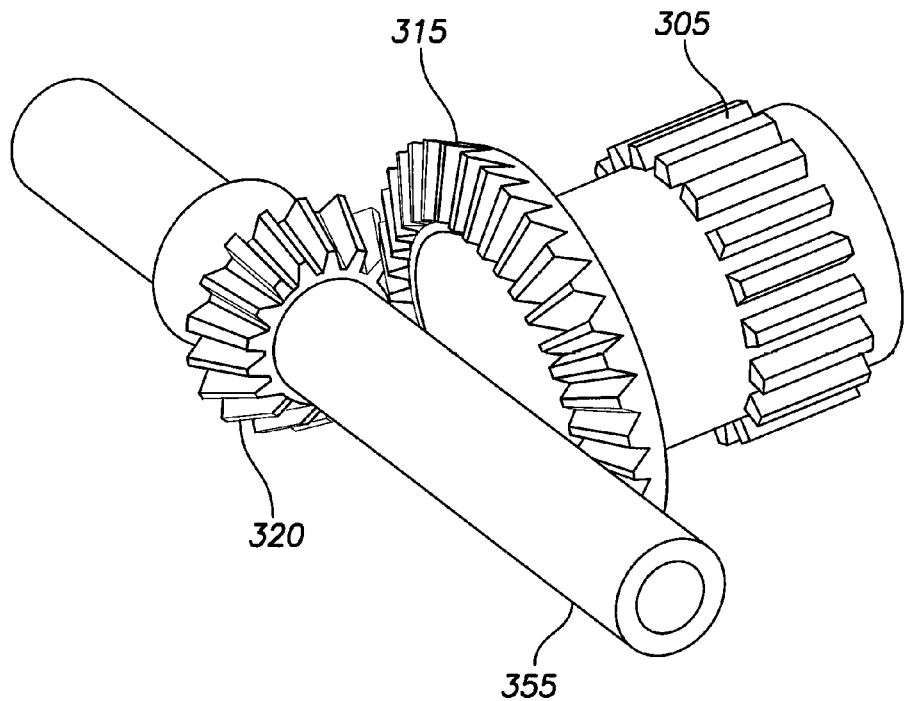
FIG. 3A is an enlarged perspective view of a pinion and perpendicular bevel gear train employed in the implant tool according to the first embodiment presented herein.

A first embodiment of an implant tool for use in connection with a lead such as lead 10 for extending and retracting helix 21 will now be described with reference to FIGS. 3 and 3A. FIG. 3 illustrates an implant tool 300 which includes an elongated housing 325 which rotatably supports a hollow shaft 355 having an axis that is longitudinally disposed with respect to housing 325. In all embodiments, reference to a "distal end" of the housing or the implant tool refers to the region where the lead is inserted into the implant tool, and reference to a "proximal end" of the housing or the implant tool refers to the longitudinally opposite end of the tool from its distal end. Housing 325 may be a two-piece housing split along the length of the implant tool 300 so as to allow the two housing halves to be assembled together along their longitudinal edges. The two housing halves may be assembled together in any manner, and preferably the housing halves are configured so as to allow press-fitting or snapping the halves together without the need for screws to assembly the housing. FIG. 3 shows implant tool 300 having half of housing 325 removed to allow illustration of parts disposed therein. Housing 325 may be fabricated of any sturdy material such as a molded plastic, and hollow shaft 355 may also be fabricated of any sturdy material such as metal or molded plastic. In general, the materials for the parts of any embodiment of the implant tool presented herein may be chosen to permit the implant tool to be cost-effectively manufactured for a one-time use prior to disposal.

Hollow shaft 355 includes a lead attachment portion 356 at its distal end for receiving a connector pin of a lead such as connector pin 25 of lead 10 described above. The connector pin is inserted into lead attachment portion 356 and coupled thereto such that the connector pin is rotatable with hollow shaft 355. A portion of a stylet (not shown) may be housed in hollow shaft 355, and a gripping handle at a proximal end of the stylet may protrude from a proximal end of hollow shaft 355 to allow the stylet to be held and maneuvered by the surgeon. The connector pin may be securely coupled to lead attachment portion 356 by an interference fit or, as shown in FIG. 3, a thumb screw or set screw 310 may be employed to lock the connector pin to hollow shaft 355. As discussed above, rotation of connector pin 25 extends or retracts helix 21, and therefore, when connector pin 25 is coupled to implant tool 300, rotation of hollow shaft 355 effects extension and retraction of helix 21. Housing 325 includes a header portion 326 having a cavity 360 for receiving connector boot 26. An interference fit between cavity 360 in the housing and connector boot 26 keeps the lead, including connector ring 27 (not visible), from rotating during connector pin rotation. A thumb screw, such as thumb screw 512 provided in a later discussed embodiment shown in FIG. 5 may also be included to lock connector boot 26 to housing 325 during connector pin rotation.

To facilitate proper rotation of the connector pin, implant tool 300 includes a shaft rotation mechanism to allow rotation of hollow shaft 355 through a predetermined amount of angular travel. For implant tool 300, the shaft rotation mechanism is a gear train which includes a rack 340 supported by housing 325 and a pinion 305, a first bevel gear 315 coupled to pinion 305 such that it rotates with pinion 305, and a second bevel gear 320 non-relatively rotatably coupled to and coaxial with hollow shaft 355 and meshing with first bevel gear 315. "Non-relatively rotationally coupled to" as used herein refers to being coupled such that the gear (or a first part as the case may be) rotates with, and not relative to, the shaft (or a second part). Pinion 305 and first bevel gear 315 have axes of rotation perpendicular to the axes of rotation of second bevel gear 320 and hollow shaft 355, and accordingly first bevel gear 315 and second bevel gear 320 mesh perpendicularly. An enlarged view of a configuration of pinion 305 sharing a common shaft with first bevel gear 315, and second bevel gear 320 on hollow shaft 355 meshing with first bevel gear 315 is shown in FIG. 3A. The shaft rotation mechanism is actuated by a control tab 330 which is coupled to rack 340. Control tab 330 is slidably supported by housing 325 such that longitudinal movement of control tab 330 in the direction of the arrow shown in FIG. 3 correspondingly moves rack 340 longitudinally, causing pinion 305 to rotate in a first direction which in turn rotates the bevel gear train, thereby rotating hollow shaft 355. Control tab 330 may then be slid back in the opposite direction to rotate hollow shaft 355 in a direction opposite the first direction.

Figure 4:
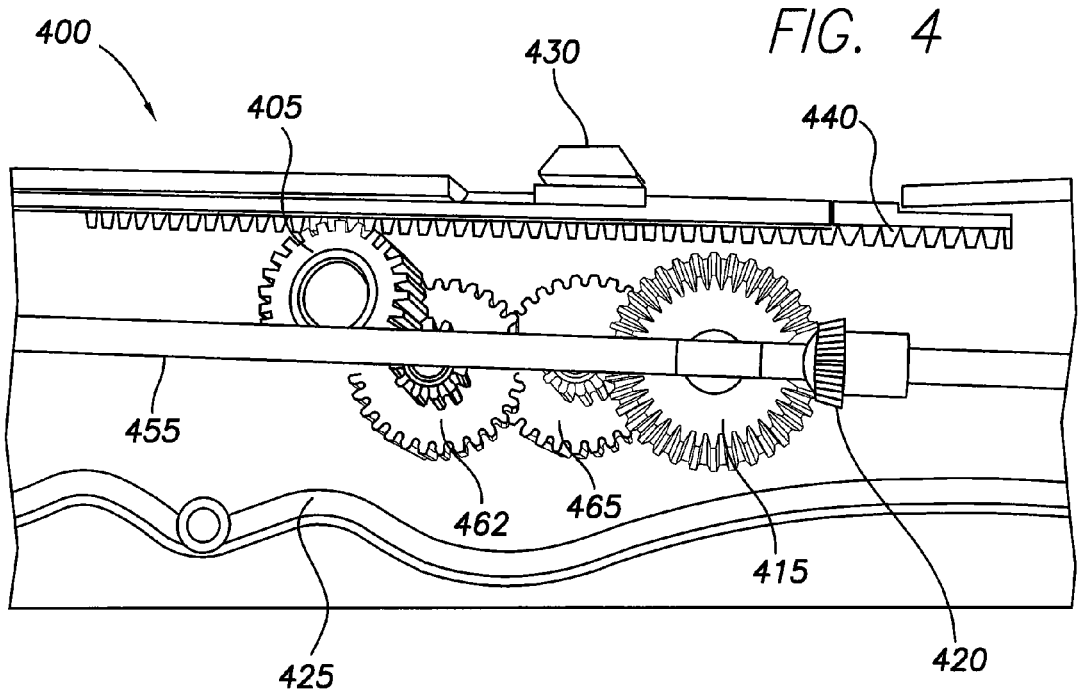
FIG. 4 is a side perspective view of an implant tool according to a second embodiment presented herein, wherein a portion of a housing is cutaway to show mechanical parts of the implant tool.

In a second embodiment, the implant tool may include additional gear stages in the gear train, such as shown in FIG. 4. FIG. 4 shows a portion of an implant tool 400 which is similar to implant tool 300 but having two additional gear stages between a pinion 405 and the bevel gear train consisting of perpendicular first and second bevel gears 415 and 420. Additional gear stages provide increased angular travel of hollow shaft 455 than that of hollow shaft 355 for the same longitudinal translation of the control tab. For example, longitudinal movement of control tab 330 of about 2 inches may correspond to about 10 revolutions of hollow shaft 355, whereas the same longitudinal movement of a control tab 430 of implant tool 400 with additional gear stages may correspond to about twice as many revolutions of hollow shaft 455.

Control tab 430 is slidably supported by a housing 425 and coupled to a rack 440 which engages pinion 405. Pinion 504 rotates a first gear stage 462 which in turn rotates a second gear stage 465. Although not fully shown, pinion 405 meshes with a small gear of first gear stage 462 which has a common shaft so as to rotate with a large gear which meshes with a small gear (not shown) of second gear stage 465. The small gear of second gear stage 465 has a common shaft so as to rotate with a large gear of second gear stage 465 which meshes with a small gear (not shown) which has a common shaft with first bevel gear 415. The gears other than the bevel gears may be any gear type configured for meshing gears having parallel axes, such as spur or helical gears, for example, and all gears may be fabricated of any sturdy material such as metal or molded plastic. Thus, longitudinal movement of control tab 430 actuates the gear train from rack 440 to pinion 405, to first and second gear stages 462 and 465, respectively, to a third gear stage including first bevel gear 415, to finally second bevel gear 420, which is non-relatively rotatably coupled to and coaxial with hollow shaft 455, thereby rotating hollow shaft 455.

Figure 5:
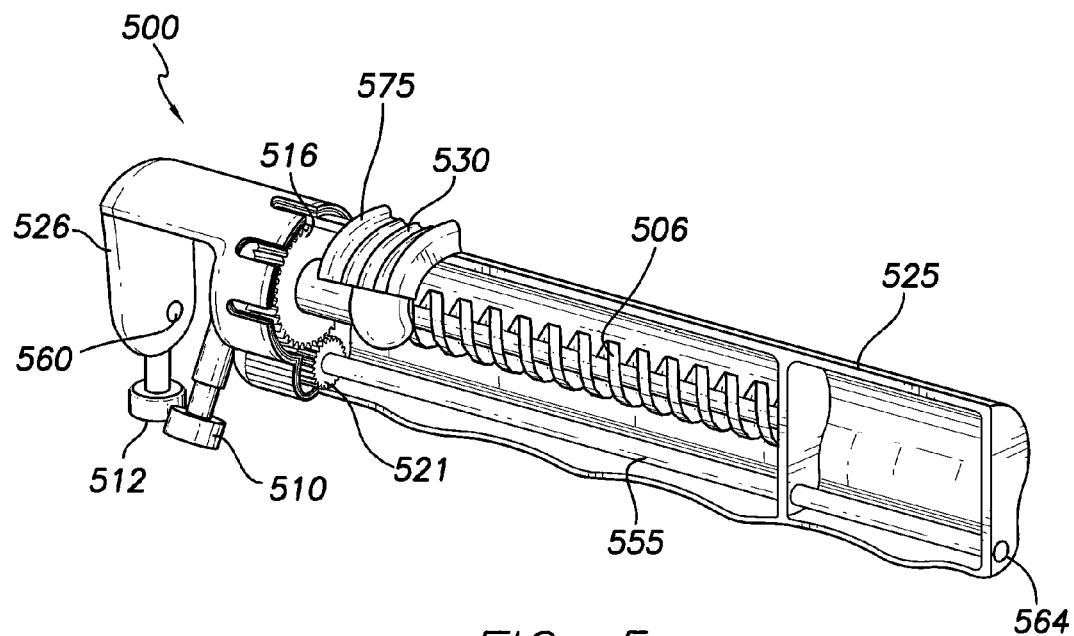
FIG. 5 is a side perspective view (with interior parts visible) of an implant tool according to a third embodiment presented herein.
Figure 5A:
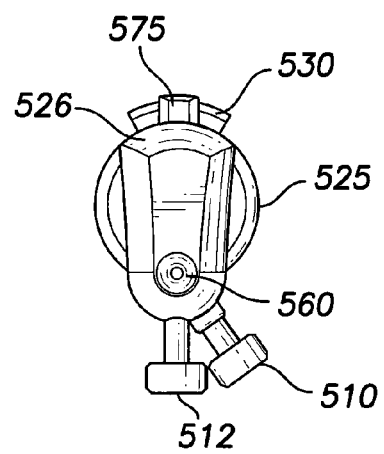
FIG. 5A is a front perspective view of the implant tool shown in FIG. 5.

A third embodiment of an implant tool for extending and retracting helix 21 will now be described with reference to FIGS. 5 and 5A. FIG. 5 illustrates an implant tool 500 (with interior parts visible) which is similar in many respects to implant tool 300 but employs a shaft rotation mechanism utilizing a gear train including a worm gear to rotate a hollow shaft 555. Implant tool 500 includes a housing 525, which may be a two-part housing as described above with respect to implant tool 300, and a header housing 526 having a cavity 560 for receiving a connector boot of a lead. Header housing 526 is detachably coupled, such as being press-fitted, for example, to a distal end of housing 525. Alternatively, header housing 526 may be integral with housing 525 such as provided in a later discussed embodiment shown in FIG. 6.

In this embodiment, a thumb screw 512 is receivable within header portion 526 to lock connector boot 26 to housing 525 during connector pin rotation. Alternatively, an interference fit between cavity 560 in the housing and the connector boot may be employed without the use of a thumb screw to keep the lead body (and connector ring) from rotating during connector pin rotation. A second thumb screw 510 may be employed on a distal end of hollow shaft 555 having a lead attachment portion (not shown), similar to lead attachment portion 356 of implant tool 300 shown in FIG. 3, for securely coupling connector pin 25 to hollow shaft 555. Alternatively, an interference fit without use of a thumb screw, as provided in the later discussed embodiment shown in FIG. 6, may be employed to lock the connector pin to hollow shaft 555. FIG. 5A shows a front perspective view of implant tool 500, including thumb screws 510 and 512 and cavity 560 in header portion 526 of housing 525. Cavity 560 aligns with the interior of hollow shaft 555 and a stylet receiving cavity 564 at a proximal end of hollow shaft 555. Stylet receiving cavity 564 permits the surgeon to insert a stylet from a proximal end of implant tool 500 through hollow shaft 555 into the lead attachment portion toward a distal end of implant tool 500. A gripping handle of the stylet to be held by the surgeon may protrude from a proximal end of hollow shaft 555.

The shaft rotation mechanism employed in implant tool 500 includes an input member 541 coupled to a control tab 530 slidably supported by housing 525, a worm gear 506 supported by housing 525 which meshes with input member 541, an input gear 516 which has a common shaft with worm gear 541 so as to rotate with a worm gear 541, and an output gear 521 which meshes with input gear 516. The shaft of worm gear 541 and input gear 516 is parallel with hollow shaft 555. Output gear 521 is non-relatively rotatably coupled to and coaxial with hollow shaft 555 such that rotation of output gear 521 rotates hollow shaft 555 (and the lead attachment portion which receives the connector pin of the lead, not shown in the view of FIG. 5). Like the gear train of implant tools 300 and 400, the gear train of implant tool 500 is actuated by longitudinal movement of control tab 530. Input member 541 is moved with control tab 530 along worm gear 506 causing worm gear 506 to rotate which in turn rotates input gear 516. Input gear 516 meshes with output gear 521 causing output gear 521 to rotate, thereby rotating hollow shaft 555. Input gear 516 and output gear 521 may be any gear type configured for meshing gears having parallel axes. In one embodiment, one revolution of input gear 516 corresponds to at least four revolutions of output gear 521. A similar gear ratio may be employed in the bevel gear train of implant tools 300 and 400. In implant tool 400, one revolution of pinion 405 may correspond to an even greater number of revolutions of second bevel gear 420, such as, for example, between 6-8 revolutions, due to the additional gear stages employed in the gear train.

Implant tool 500 may also include a stop 575 coupled to housing 525 to engage control tab 530 along its longitudinal path of travel so as to limit the control tab's sliding distance and therefore limit the amount of angular travel of hollow shaft 555. Stop 575 may be fixed in a position on housing 525 or may be adjustably set to a position on housing 525 so as to adjust the control tab's sliding distance and angular travel of the hollow shaft. Adjustability of stop 575 is unnecessary where the implant tool is manufactured for one-time use. Lack of adjustability of stop 575 would also reduce the risk of error in setting the number of rotations. Accordingly, different one-time use models of the implant tool may be manufactured to accommodate different size leads having varying rotational requirements to properly extend and retract the helix. Stop 575 may also be employed on any of the other implant tool embodiments presented herein. Stop 575 is not essential for limiting a control tab's sliding distance since the sliding distance may also be limited by abutment of the control tab against the housing. Other types of stops, or stopping means, may also be used, such as a stopper tab or "brake" on one of the gears.

In each embodiment, the control tab is slidable over a predetermined distance, and/or the angular travel of the hollow shaft is set to a predetermined amount to facilitate proper rotation of the connector pin and therefore ensure fixation of the helix to the body tissue position. In one embodiment, for example, the predetermined sliding distance of the control tab is between one and two inches. In another embodiment, the predetermined amount of angular travel of the hollow shaft is within the range of 2880-7200°.

A fourth embodiment of an implant tool for extending and retracting helix 21 will now be described with reference to FIGS. 6 and 6A-6C. FIGS. 6 and 6A-6C show an implant tool 600 which is similar to implant tool 500 but having a single thumb screw 612 and no hollow shaft extending between the implant tool's distal and proximal ends. Rather, implant tool 600 includes output gear 621 having a short hollow shaft supported by a housing 625 of implant tool 600 and non-relatively rotatably coupled to a proximal end of a lead attachment portion 656. Housing 625 includes a longitudinal groove or tunnel 670 formed in the housing between, and aligned with, the hollow shaft of output gear 621 and a stylet receiving cavity 664 at the proximal end of implant tool 600. The surgeon inserts a stylet into stylet receiving cavity 664 through tunnel 670, through the hollow shaft of output gear 621, and into lead attachment portion 656. A thumb screw or set screw 614 is receivable within the proximal end of housing 625 near the stylet receiving cavity 664 for locking the stylet to the housing to prevent its slippage in the lead during implant. A connector pin of a lead is inserted into lead attachment portion 656 and coupled thereto by an interference fit such that the connector pin is rotatable with the hollow shaft of output gear 621.

Housing 625 may be a two part housing as shown in FIGS. 6 and 6C which may be attached together by press fitting, for example, or by other means as would be apparent to one skilled in the relevant art. Housing 625 has a header portion 626 having a cavity 660 which aligns with the interior of lead attachment portion 656 and tunnel 670 as shown in the front perspective view of implant tool 600 of FIG. 6A. Cavity 660 receives connector boot 26 of the lead which is locked to housing 625 using thumb screw 612 so that the connector pin rotates without also rotating the lead body.

A shaft rotation mechanism for rotating lead attachment portion 656 includes a control tab 630, an input member 641, a worm gear 606, an input gear 616, and output gear 621. Rotation of output gear 621 rotates lead attachment portion 656 non-relatively rotatably coupled to the hollow shaft of output gear 621. The shaft rotation mechanism employed in implant tool 600 is mechanically similar to that employed in implant tool 500, and therefore details of the parts and their interconnection are omitted.

A method of using implant tool 300, 400, 500, or 600 will now be described with reference to the flowchart illustrated in FIG. 9. The method includes step 90 of providing a lead extension and retraction device such as implant tool 300, 400, 500, or 600, which includes a control tab and a shaft rotating mechanism configured to rotate a shaft when the control tab is slid. In step 91, a lead that includes a helix or active fixation tip at a distal end of the lead is provided. The lead may be a coil lead as described above with reference to FIGS. 1 and 2A-2C having a connector pin at its proximal end. In step 92, the lead is non-relatively rotatably coupled at its proximal end to the shaft's distal end such that the lead's proximal end rotates with the distal end of the shaft, and in step 93, a distal end of the helix is located proximate a body tissue, such as the myocardial tissue. The implant tool is then advanced distally while simultaneously sliding the control tab distally with respect to the housing (step 94).

In another embodiment, the method further includes the step of checking the location of the implanted helix (step 95), which may include performing various electrical tests to confirm that the helix electrode is positioned at a proper tissue location. The method may further include the steps of retracting and re-locating the helix and advancing again the distal end of the helix proximate to the body tissue in order to re-position the helix at the proper tissue location. Retracting step 96 includes retracting the implant tool proximally while simultaneously sliding the control tab proximally with respect to the housing. The distal end of the helix is then re-located near the body tissue (step 93), and the implant tool is again advanced distally while simultaneously sliding the control tab distally to correspondingly rotate the helix and anchor it into the body tissue (step 94).

In any of the embodiments presented herein, it should be understood that the control tab may be slid using manual means and/or automatic means. For example, the control tab or input member may be coupled to a motor to electrically actuate shaft rotation to effect extension and retraction of an active fixation tip of a lead. In a fifth embodiment of an implant tool for extending and retracting helix 21, the shaft rotation mechanism and control tab described above in the previous embodiments is replaced by an electric motor. Accordingly, the implant tool includes a shaft (having a lead attachment portion) rotatably supported by a housing and an electric motor configured to rotate the shaft through a predetermined amount of angular travel. The electric motor may be any type of motor known in the art for operating hand-held medical devices. For example, a brush type or brush-less motor may be used, and the electric motor may be small, such a tiny DC motor used in small hand-drills, and of such a size for allowing the motor to be disposed inside the housing or suitably attached thereto. The motor may be connected to a proximal end of the shaft and driven by a battery. An encoder may be included as a speed control means of the electronic motor for controlling and reading the position of the motor. A switch or lever may be operatively connected to the electric motor so as to allow user selection of the speed and direction of angular travel of the shaft driven by the motor. Similar to the control tab of the previously described embodiments, the switch may be a sliding-type mechanism in which a speed and direction that the switch is actuated by the user, or by other means, correlates to a speed and direction that the motor rotates the shaft.

Figure 7A:
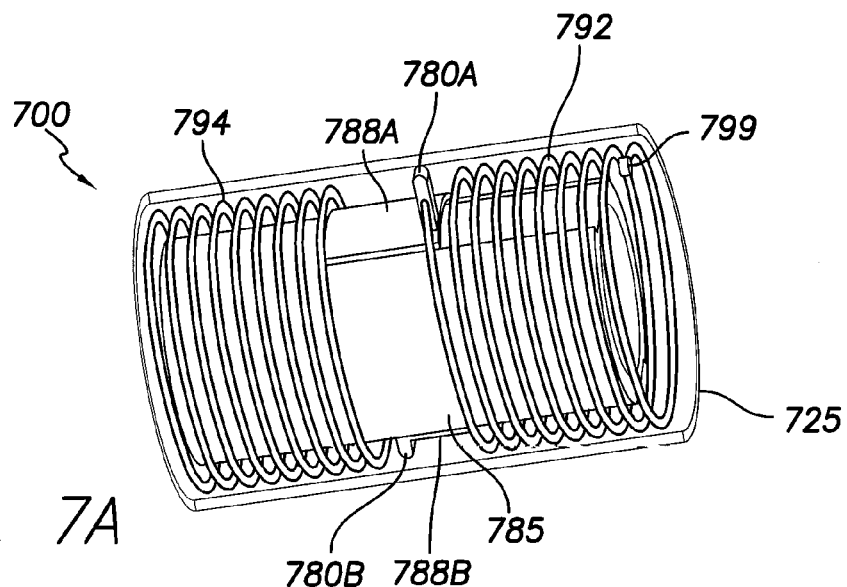
FIG. 7A is side perspective view of a shaft rotation mechanism of the implant tool according to a sixth embodiment presented herein, having a clockwise wound spring and a counter-clockwise wound spring each connected to a slider.
Figure 7B:
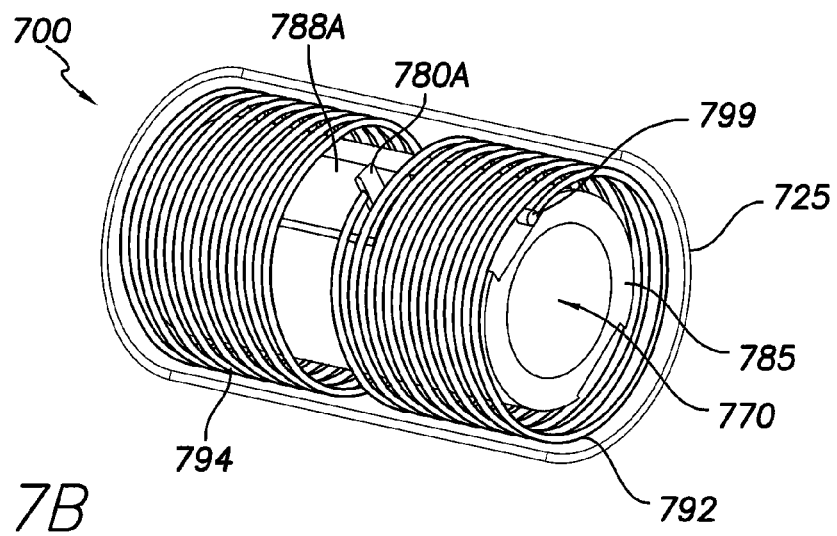
FIG. 7B is another side perspective view of the shaft rotation mechanism shown in FIG. 7A.
Figure 7C:
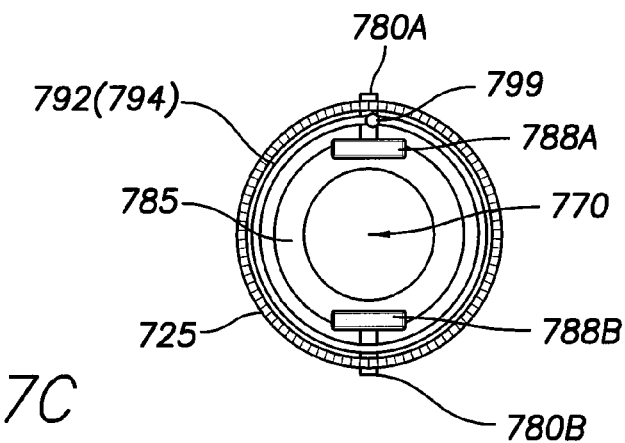
FIG. 7C is an axial view of the shaft rotation mechanism shown in FIG. 7A.

A sixth embodiment of an implant tool for extending and retracting helix 21 will now be described with reference to FIGS. 7A-7C. FIGS. 7A and 7B show side perspective views of a shaft rotation mechanism of an implant tool 700. FIG. 7C shows an axial view of the shaft rotation mechanism of implant tool 700. Implant tool 700 has a device housing 725, which may be similar to the other embodiments presented herein and may likewise include a header housing (though not shown), such as header housing 526 of implant tool 500, and one or more thumb screws to fasten the connector boot and/or connector pin to the implant tool, similar to the thumb screws 510 and 512 of implant tool 500, for example. Implant tool 700 includes a shaft or internal cylinder 785 which is rotatably supported by housing 725 and has a lead attachment portion (not shown), which may be similar to lead attachment portions shown in FIG. 3, 5 or 6, for receiving a connector pin of a lead such that it is rotatable with internal cylinder 785. Internal cylinder 785 may include an inner lumen 770 through which a lead stylet passes, similar to the hollow shaft of earlier described embodiments.

The shaft rotation mechanism includes a double acting spring mechanism and actuation mechanisms 780a and 780b for actuating the double acting spring mechanism. The double acting spring mechanism has opposing right (clock-wise) and left (counter-clockwise) wound torque springs 792 and 794, respectively, which are each respectively connected to single actuating sliders 788a and 788b, which in turn are non-relatively rotatably connected to internal cylinder 785. Sliders 788a and 788b may include a first portion that is set in a groove provided along internal cylinder and a second portion connected to respective actuation mechanisms 780a and 780b. When actuated, sliders 788a and 788b are driven by respective springs 792 and 794, thereby engaging and rotating internal cylinder 785 in respective clock-wise direction R and counter-clockwise direction L. For each slider/spring combination, one end of spring 792 or 794 is connected to slider 788a or 788b and the other end of the spring has a portion fixed to housing 725, such as fixed portion 799 shown in FIG. 7B for spring 792.

The springs may be a commodity or off-the-shelf part, thereby simplifying manufacturing and minimizing parts costs. The double acting spring mechanism functions to automate extension and retraction of a helix without requiring a user to supply the torque to effect rotation of the lead. Left and right wound springs 794 and 792 may be disposed adjacent to each other as shown in FIGS. 7A and 7B, or alternatively, the springs may be disposed one inside the other, wherein one of the left and right wound springs has a smaller wound diameter than the other of the left and right wound springs. Oppositely wound springs 792 and 794 will stabilize each other and permit the helix to be extended and retracted alternately and repeatably with alternate operation of actuation mechanisms 780a and 780b. The double acting spring mechanism should provide little to no backlash, which may be associated with a gear train type of shaft rotation mechanism.

Actuation mechanisms 780a and 780b may each be a woodruff key or push button, for example, as shown in FIGS. 7A-7C, wherein operation of the actuation mechanism is a pushing motion. Operation of one of actuation mechanism 780a or 780b releases one of springs 792 or 794, and consecutive operation of the other of actuation mechanism 780b or 780a releases the other of the springs 794 or 792. Actuation mechanisms 780 a or 780b are thus configured to alternately release the right and left hand wound springs 792 and 794. For example, when actuation mechanism 780a is pressed, right hand wound spring 792 may be released, thereby rotating slider 788 in a clockwise direction. Slider 788a in turn rotates internal cylinder 785 clockwise, which will cause a connector pin non-relatively rotatably connected thereto to rotate clockwise and extend a helix. When actuation mechanism 780b is consecutively pressed, left hand wound spring 794 would be released, which turns slider 788b in a counter-clockwise direction, which in turn causes internal cylinder 785 to rotate counter-clockwise. The connector pin coupled to internal cylinder 785 would also be rotated counter-clockwise, causing the helix to be retracted.

Instead of two single actuating sliders, it should be apparent that a single double actuating slider (not shown) may be used that is connected to a single actuation mechanism (not shown) configured to alternately release the right and left hand wound springs 792 and 794. For example, when the actuation mechanism is pressed a first time, right hand wound spring 792 is released, thereby rotating the slider in a clockwise direction and translating it to engage with left hand wound spring 794, and when the actuation mechanism is pressed a second time, left hand wound spring 794 is released, thereby rotating the slider in a counter-clockwise direction and translating it to engage with right hand wound spring 792.

Figure 8A:
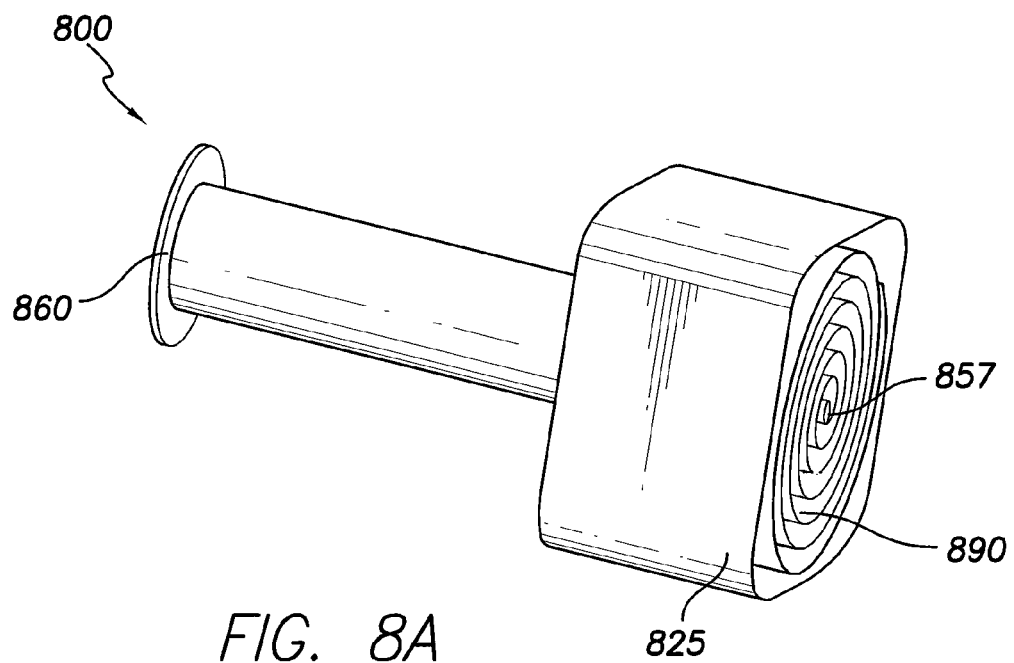
FIG. 8A is a side perspective view of an implant tool according to a seventh embodiment presented herein.
Figure 8B:
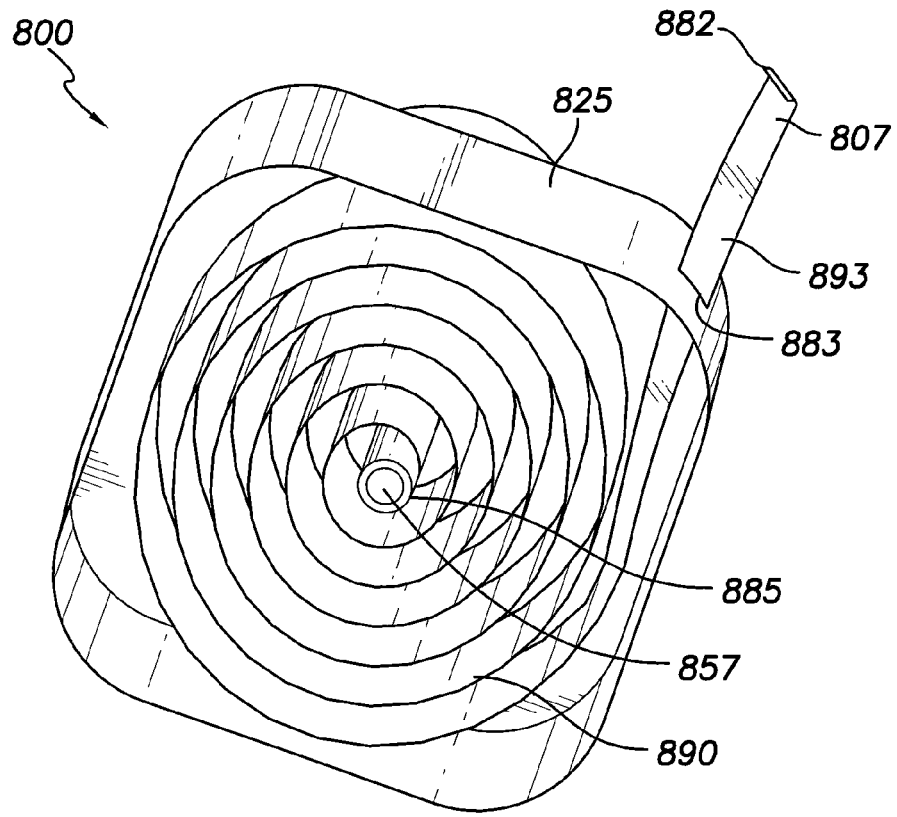
FIG. 8B is a front perspective view (with certain interior parts made visible) of the implant tool shown in FIG. 8A.
Figure 8C:
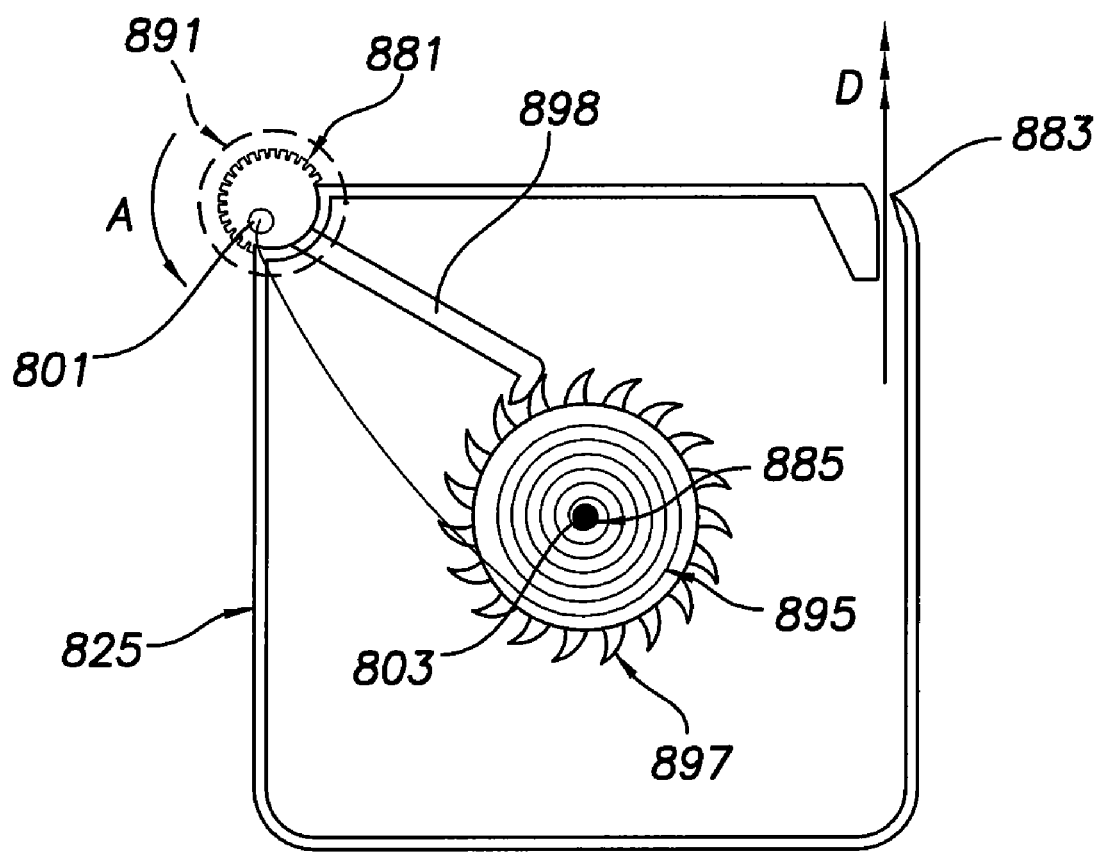
FIG. 8C is another front perspective view showing a locking mechanism and a release mechanism of the implant tool shown in FIG. 8A.

A seventh embodiment of an implant tool for extending and retracting helix 21 will now be described with reference to FIGS. 8A-8C. FIGS. 8A and 8B show side and front views, respectively, of an implant tool 800 having a shaft rotation mechanism disposed in a device housing 825. The shaft rotation mechanism includes a retractable tape 890 wound around a rotatable shaft or internal cylinder 885, which is supported by housing 825. Internal cylinder 885 rotates in a first direction when tape 890 is unwound, and rotates in a second direction when tape 890 is retracted or rewound. Housing 825 includes a connector boot cavity 860 for receiving a lead connector boot, and internal cylinder 885 includes a lead attachment portion 857 for selectively and non-relatively rotatably coupling a lead connector pin to the internal cylinder. Internal cylinder 885 may also include a stylet receiving cavity, similar to that shown in FIG. 5 for implant tool 500, which is accessible from the cylinder's proximal end for insertion of a stylet into the lead connector pin. Connector boot cavity 860 may provide an interference fit to lock the connector boot to the housing to prevent rotation of the connector boot during rotation of the connector pin. Other attachment means, such as set pin or thumb screw to secure the connector boot in cavity 860 and similar means for securing the connector pin to lead attachment portion 857 may also be used. A header housing configuration, such as header housing 526 in FIG. 5 may be used in connection with the shaft rotation mechanism shown in FIGS. 8A-8C.

Tape 890 has a first end secured via a rotatable bushing to internal cylinder 885 and a second, free end 893 extending through a tape opening or cavity 883 in housing 825. Second end 893 has an end stop 882 which may rest at opening 883 so as to prevent tape 890 from retracting entirely within housing 825. End stop may be a metal or plastic tab, for example, that may be pulled by a surgeon to unwind tape 890. The arrows D shown in FIGS. 8B and 8C illustrate a direction in which tape 890 may be pulled by its second end 893 to remove it from housing 825.

Implant tool 800 may further include an auto-retraction mechanism to allow any unwound length of tape 890 to be retracted into housing 825. The auto-retraction mechanism may be similar to a self-winding measuring tape or car seat belt in construction and function. In one embodiment, the auto-retraction mechanism includes a coiled spring 895 which is tensioned when tape 890 is unwound and loads a ratchet wheel 897 non-relatively rotatably coupled to internal cylinder 885. Coiled spring 895 includes a first end 801 fixed to a stationary point, such as a later described release mechanism 891, as shown in FIG. 8C, or housing 825, and a second end 803 fixed to internal cylinder 885. A pawl 898 engaging with ratchet wheel 897 together constitute a locking mechanism to hold internal cylinder 885 in a position and prevent retraction of tape 890. A release mechanism 891 connected to pawl 898 has a tab or button 881 on housing 825 which may be actuated in a direction shown by arrow A to selectively release pawl 898 from ratchet wheel 897, relieving the tension in the spring, and permitting the spring-loaded ratchet wheel 897 to rotate internal cylinder 885 so as to auto-retract the unwound length of tape 890.

In use, an active fixation lead is coupled to lead attachment portion 857 of implant tool 800, and a surgeon pulls end stop 882 to remove tape 890 from housing 825. Unwinding tape 890 rotates internal cylinder 885 and lead attachment portion 857 in the first direction which rotates the lead connector pin, thereby extending the helix of the lead. The auto-retraction, locking, and release mechanisms allow user control of the retraction of the helix, which retracts when internal cylinder 885 is rotated in the second direction to rewind tape 890, as described above. The total number of rotations of the connector pin (and the amount of angular travel of internal cylinder 885) may be controlled and predetermined by setting the length of tape to be unwound. The shaft rotation mechanism may be scaled so that a predetermined length of tape corresponds to a single rotation of the internal cylinder. For example, a ratio of tape unwound length to one rotation of the internal cylinder may be set to be 0.5 inches. Moreover, tape 890 may be provided with a measurement indicator 807 which informs the surgeon of the number of rotations of internal cylinder 885 that have resulted during removal of tape 890 from housing 825.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A lead extension and retraction device, comprising:
a housing having a tape opening;
a shaft rotatably supported by the housing, the shaft including a lead attachment portion configured to selectively couple a lead to the shaft such that the lead is rotatable with the shaft;
a shaft rotation mechanism configured to rotate the shaft through a predetermined angular travel with respect to the housing, wherein the shaft rotation mechanism comprises:
a retractable tape positioned within the housing and wound around the shaft, the tape having a first end secured to the shaft and a second end extending through the tape opening so as to allow the second end to be selectively pulled away from the housing, wherein the tape is configured to unwind from and rotate the shaft when the second end is pulled away from the housing;

a tape auto-retraction mechanism including a coiled spring configured to be tensioned when the tape is unwound and which allows the tape to rewind around the shaft when the tension is relieved;

a locking mechanism including a ratchet wheel non-relatively rotatably coupled to the shaft and a pawl configured to selectively engage the ratchet wheel so as to lock the ratchet wheel and the shaft in a position relative to the housing to prevent auto-retraction of an unwound length of tape; and a release mechanism positioned on the housing and connected to the pawl, the release mechanism being configured to selectively release the pawl from the ratchet so as to allow the tape auto-retraction mechanism to retract the unwound length of tape.

2. The device according to claim 1, wherein the tape has a predetermined unwound length and the predetermined angular travel of the shaft is limited by the predetermined unwound length of tape.

3. The device according to claim 1, wherein the tape has indicators marked on a surface of the tape which inform the surgeon of the number of rotations of the shaft that have resulted during removal of tape from the housing.

* * * * *